US00PP28331P3

(12) United States Plant Patent
Olesen

(10) Patent No.: US PP28,331 P3
(45) Date of Patent: Aug. 29, 2017

(54) FLORIBUNDA ROSE PLANT NAMED 'POULNAP005'

(50) Latin Name: ***Rosa* hybrid**
Varietal Denomination: Poulnap005

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 82 days.

(21) Appl. No.: 14/756,277

(22) Filed: Aug. 20, 2015

(65) Prior Publication Data

US 2017/0055401 P1 Feb. 23, 2017

(51) Int. Cl.
*A01H 5/02* (2006.01)

(52) U.S. Cl.
USPC ..... Plt./146

(58) Field of Classification Search
USPC ..... Plt./146
See application file for complete search history.

(56) References Cited

PUBLICATIONS

National Parks Perfection by Poulsen, Abisco Poulnap005, http://www.poulsenroser.com/media/73107/National-PARKS-2013_LR_Poulsen-Roser_DEM.pdf, Apr. 2013.*
UPOV hit on Floribunda rose named 'Poulnap005', QZ PBR 43377, Dec. 15, 2014.*

* cited by examiner

*Primary Examiner* — Anne Grunberg

(57) ABSTRACT

A new garden rose plant of the Floribunda class which has abundant, orange red flowers and attractive foliage. This new and distinct variety has shown to be uniform and stable in the resulting generations from asexual propagation.

1 Drawing Sheet

Botanical designation: *Rosa* hybrid.
Variety denomination: 'Poulnap005'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2004 and the resulting seeds were planted in a controlled environment in Fredensborg, Denmark. The new variety, named 'Poulnap005', originated as a single seedling from the stated cross.

The new variety may be distinguished from its male pollen parent and female seed parent primarily by the following characteristics. The female seed parent has red flowers, while the new variety has orange red flowers. The male pollen parent has yellow flowers, while the new plant has orange red flowers.

The objective of the hybridization of this rose variety was to create a new and distinct variety for garden use with unique qualities, such as:

1. Uniform and abundant orange red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulnap005' from all other varieties of which we are aware.

As part of the rose development program, Mogens N. Olesen germinated the seeds from the aforementioned hybridization during winter of 2004 and conducted evaluations on the resulting seedlings in a controlled environment in Fredensborg, Denmark. 'Poulnap005' was selected in the spring of 2005 by the inventor as a single plant from the progeny of the aforementioned hybridization.

Asexual reproduction of 'Poulnap005' by traditional budding and rooted cuttings was first done by Mogens N. Olesen in the nursery in Fredensborg, Denmark in July, 2005. This initial and other subsequent asexual propagations conducted in controlled environments have demonstrated that the characteristics of 'Poulnap005' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulnap005'. Specifically illustrated in the drawing are open flowers at various stages of development, flower petals detached, reproductive flower parts, mature leaf, and bare stems. Plants shown are 2 years of age.

DETAILED DESCRIPTION OF THE VARIETY

The following is a description of 'Poulnap005', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulriber', U.S. Plant Pat. No. 12,902 are compared to 'Poulnap005' in Chart 1.

CHART 1

| | 'Poulnap005' | 'Poulriber' |
|---|---|---|
| Petal Count | 25 to 30 | 18-22 petals |
| Flower Diameter | 80 mm | 65-75 mm |
| General Tonality of Flower Color | Orange Red Group N30A | Red Group 40C-41B |

Flower and Flower Bud

Blooming habit: Continuous.

Flower bud:

*Size.*—Upon opening, 30 mm in length from base of receptacle to end of bud. Bud diameter is 15 mm.

*Bud form.*—Ovoid.

*Bud color.*—As sepals divide petals are Orange-Red Group 34A and Yellow Group 12A.

*Sepal inner surface.*—Color: Yellow-Green Group 147D with intonations of Greyed-Red Group 182A. Surface: Lightly pubescent.

*Sepal outer surface.*—Color: Yellow-Green Group 144A with strong intonations of Greyed-Red Group 178B. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—30 mm long, 8 mm wide.

*Receptacle.*—Texture: Smooth. Size: 8 mm in height, 10 mm wide. Color: Yellow-Green Group 144A with intonations of Greyed-Red Group 178B. Shape: Campanulate.

*Pedicel.*—Surface: Smooth. Length: 40 mm. Diameter: 3 mm on average. Color: Yellow-Green Group 144A. Strength: Moderately strong.

Flower bud development: Flower buds are borne in clusters of 3 to 5 flower buds per stem.

Flower bloom:

*Fragrance.*—None.

*Duration.*—The blooms have a duration on the plant of approximately 14 days. Petals fall cleanly away from plant after flowers have fully matured.

*Size.*—Flower diameter is about 80 mm when open. Flower depth is 30 mm.

*Flower shape.*—Rosette, double flower with many slightly overlapping petals of different sizes.

*Shape of flower, side view.*—The upper portion is flattened convex. The lower portion is concave.

Petalage: Under normal conditions, flowers have 25 to 30 petals.

General tonality of flower: Open flowers are Orange-Red Group N30A. After flowers have fully matured, general tonality becomes Orange-Red Group 32C.

Petal color:

*Upon opening, outer petals.*—Upper surface: Orange-Red Group N30A. Lower surface: Red Group 43B splashed with Yellow-Orange Group 22B.

*Upon opening, inner petals.*—Upper surface: Orange-Red Group N30A. Lower surface: Red Group 43B splashed with Yellow-Orange Group 22B.

*Basal petal spots, upon opening.*—Upper surface: Yellow Group 9A. Lower surface: Yellow Group 9A.

*After opening, outer petals.*—Upper surface: Orange-Red Group 32C. Lower surface: Orange-Red Group 35B splashed with Orange-Red Group 29B.

*After opening, inner petals.*—Upper surface: Orange-Red Group 32C. Lower surface: Orange-Red Group 35B splashed with Orange-Red Group 29B.

*Basal petal spots, after opening.*—Upper surface: Yellow Group 9A. Lower surface: Yellow Group 4A.

Petals:

*Petal reflex.*—Slightly.

*Margin.*—Entire and uniform with occasional cleft. Weak undulations.

*Shape.*—Generally elliptical. Apex shape: Rounded. Base shape: Acute.

*Size.*—40 mm (l)×40 mm (w).

*Texture.*—Smooth.

*Thickness.*—Average.

Petaloids:

*Size.*—30 mm (l) by 15 mm (w).

*Quantity.*—About 5.

*Shape.*—Irregular, with acute base and rounded apex.

*Color.*—The upper surface is Orange-Red Group 32C with Yellow Group 9A at the petal base. The lower surface is Orange-Red Group 35B splashed with Orange-Red Group 29B.

Reproductive flower parts:

*Pollen.*—None observed.

*Anthers.*—Size: 2 mm in length. Color: Yellow-Orange Group 23B. Quantity: 40 on average.

*Filaments.*—Color: Yellow-Orange Group 21B. Length: 10 mm.

*Pistils.*—Length: 4 mm. Quantity: 25 on average.

*Stigmas.*—Color: Yellow Group 11B.

*Styles.*—Color: Green-White Group 157A.

*Hips.*—None Observed.

Plant

Plant growth: Upright, bushy. Plants are 65 cm in height, and 60 cm wide.

Stems:

*Color.*—Juvenile growth: Yellow-Green Group 144B with intonations of Greyed-Red Group 178A. Mature growth: Yellow-Green Group 144A.

*Length.*—On average, canes are 30 cm from the base of the plant to the flowering portion.

*Diameter.*—6 mm.

*Internodes.*—On mature canes about 50 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 9 mm.

*Shape.*—Upper portion is convex. Lower portion is concave.

*Color.*—Juvenile prickles: Greyed-Red Group 182A. Mature prickles: Greyed-Red Group 182A.

Plant foliage:

*Compound leaf.*—150 mm (l)×110 (w).

*Quantity.*—2 leaves per 10 cm of stem on average.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 146B.

Plant leaves and leaflets:

*Stipules.*—Size: 22 mm long, 7 mm wide. Quantity: 2 per compound leaf. Shape: Linear, slightly broad based with outward extending apices. Margins: Finely serrated. Color: Yellow-Green Group 144A.

*Petiole.*—Length: 20 mm. Diameter: 2 mm.

*Upper surface.*—Color: Yellow-Green Group 144B.

*Lower surface.*—Color: Yellow-Green Group 144A.

*Rachis.*—Length: About 75 mm. Upper surface: Color: Yellow-Green Group 144B.

*Lower surface.*—Color: Yellow-Green Group 144A.

*Leaflet.*—Quantity: Normally 5 leaflets. Margins: Serrated. Size: On average terminal leaflets are 65 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Floribunda rose class named 'Poulnap005', substantially as illustrated and described herein, due to its abundant orange red flowers, disease resistance, and extended period of bloom.

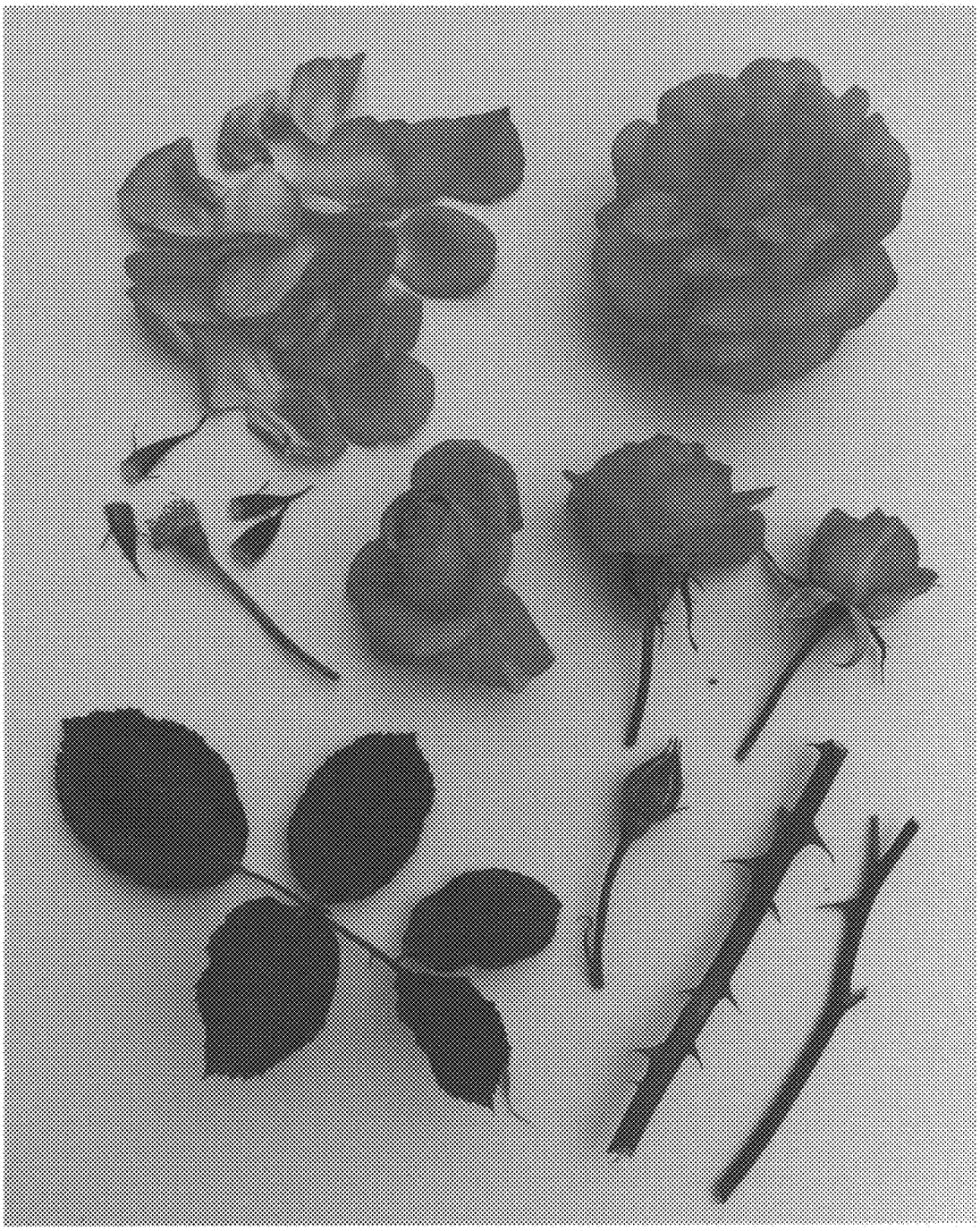

* * * * *